United States Patent [19]

Taddei

[11] Patent Number: 4,664,656
[45] Date of Patent: May 12, 1987

[54] INJECTION SYRINGE

[76] Inventor: André Taddei, 32 Rue Centrale, Nice - Alpes Maritimes, France

[21] Appl. No.: 727,897

[22] Filed: Apr. 26, 1985

[30] Foreign Application Priority Data

Apr. 26, 1984 [FR] France ................................ 8406907

[51] Int. Cl.[4] ........................................... A61M 5/325
[52] U.S. Cl. .................................................... 604/241
[58] Field of Search .................. 604/241, 88, 232, 187

[56] References Cited

U.S. PATENT DOCUMENTS

| 2,483,825 | 10/1949 | Goldberg | 604/241 |
| 2,672,867 | 3/1954 | Ashkenaz | 604/241 |
| 2,778,359 | 1/1957 | Friedman | 604/241 |
| 3,092,108 | 6/1963 | Friedman | 604/241 |
| 3,967,621 | 7/1976 | Schwarz | 604/241 |

Primary Examiner—John D. Yasko
Attorney, Agent, or Firm—Harry M. Weiss & Associates

[57] ABSTRACT

An improved injection syringe device for use especially by dental surgeons is disclosed. The needle assembly tip of said improved injection syringe device has a male threaded portion which can fit into the internally threaded portion of a hollow sleeve integrally connected at the bottom on a housing forming the syringe. The top of the needle assembly is thus guided and protected before passing through the orifice without touching the edges of the sleeve by screwing said needle assembly into said sleeve. Upon completion of the placement of said needle assembly into said sleeve, a plug between the housing and the sleeve is pierced; thus, permitting fluid contained within said housing to be injected through said needle assembly.

1 Claim, 10 Drawing Figures

U.S. Patent   May 12, 1987   Sheet 1 of 3   4,664,656
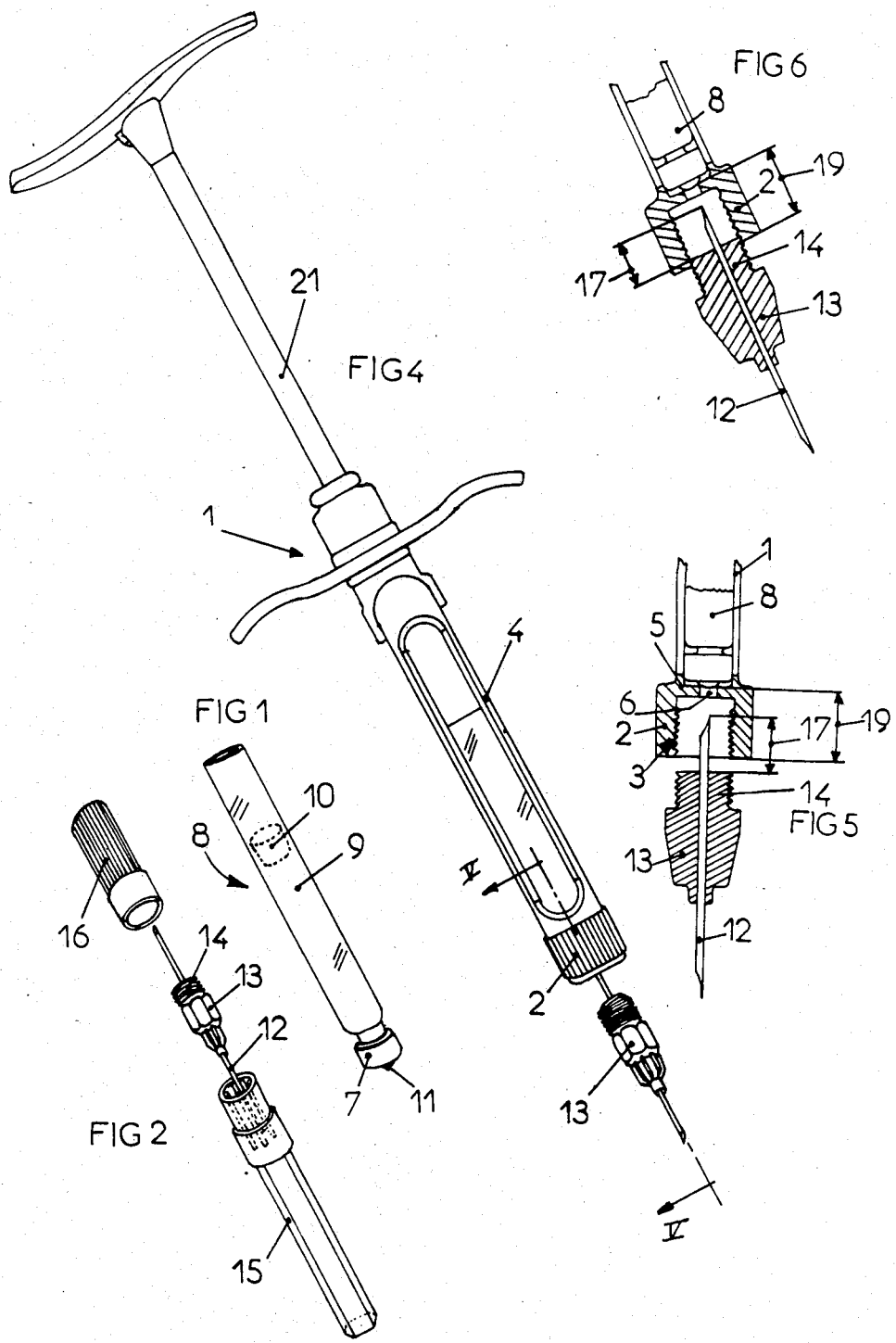

INJECTION SYRINGE

BACKGROUND OF THE INVENTION

This invention concerns an injection syringe device to be utilized especially by dentists to give injections inside the mouths of their patients.

It is well known, especially for dental surgeons, that injections are very frequent surgical procedures, particularly to administer local anesthesia. A dentist, for example, would insert a hollow needle attached to an ampule of fluid which he would then inject by means of a thrust syringe. Moreover, it is known that, because of the particular nature of the tissue into which the dentist usually makes his injections, the plunger of the syringe is activated by an extremely strong plunger-fulcrum system, thus enabling the dentist to apply a strong push to the fluid in the ampule with the palm of his hand. Accordingly, syringes of this kind include a very strong metal syring holder, the plunger of which is shaped to anatomically fit in the palm of the dental surgeon's hand.

Due to the frequency of the above-mentioned surgical procedure with the minimal amounts of anesthesia injected each time, it is clear that the dental surgeon must use the same needle a number of times and also the same ampule or cartridge a number of times. There is therefore a problem in day-to-day practice concerning compliance with sterility regulations whenever the dental surgeon changes needle. It is a fact that most of the systems known today do not allow adequate compliance with stringent regulations of asepsis.

A need is therefore felt to avoid such drawbacks by creating a needle-cartridge-syringe injection device which permits very strict compliance with the regulations of asepsis when a dental surgeon carries out the normal operations related to an injection, especially when he wishes to change the needle or the cartridge of the injection device.

SUMMARY OF THE INVENTION

It is an object of the present invention to provide an improved injection syringe which consists of a plunger syringe into the body of which the cartridge containing the fluid to be injected is inserted, while the threaded end of the syringe is capable of receiving, by threaded connection, the tip of a hollow injection needle having the threaded end of the syringe comprising a tubular sleeve threaded on the inside with the tip of the needle being a male tip, threaded on the outside, capable of fitting inside the tip of the syringe sleeve.

It is another object of this invention to provide an improved injection syringe wherein the needle extends beyond the male threaded tip by less than the distance between the top of the tip and the lower perforable end of the cartridge when the tip is positioned in front of the threaded sleeve of the syringe to permit the needle-holding tip to be centered on the end of the syringe sleeve for holding the upper end of the needle in position while said needle is being screwed on prior to piercing the rubber capsule which seals the cartridge.

It is a further object of this invention to provide an improved injection syringe in order to avoid sudden contact of the needle with the wall of said syringe to comply with regulations of asepsis.

These and other features of the invention will be understood upon reading of the following description along with the drawings.

BRIEF DESCRIPTION OF THE DRAWINGS

FIG. 1 is a perspective view of a well-known type of cartridge containing the fluid to be injected.

FIG. 2 is an exploded perspective view of a needle according to the present invention, as it is being removed from its sterile package.

FIG. 4 is a perspective view of the syringe as the needle is about to be inserted.

FIGS. 5 and 6 are cross-sectional views taken along line V—V of FIG. 4 showing two successive stages in the process of positioning the needle.

DESCRIPTION OF THE PREFERRED EMBODIMENT

Figures 3, 7:
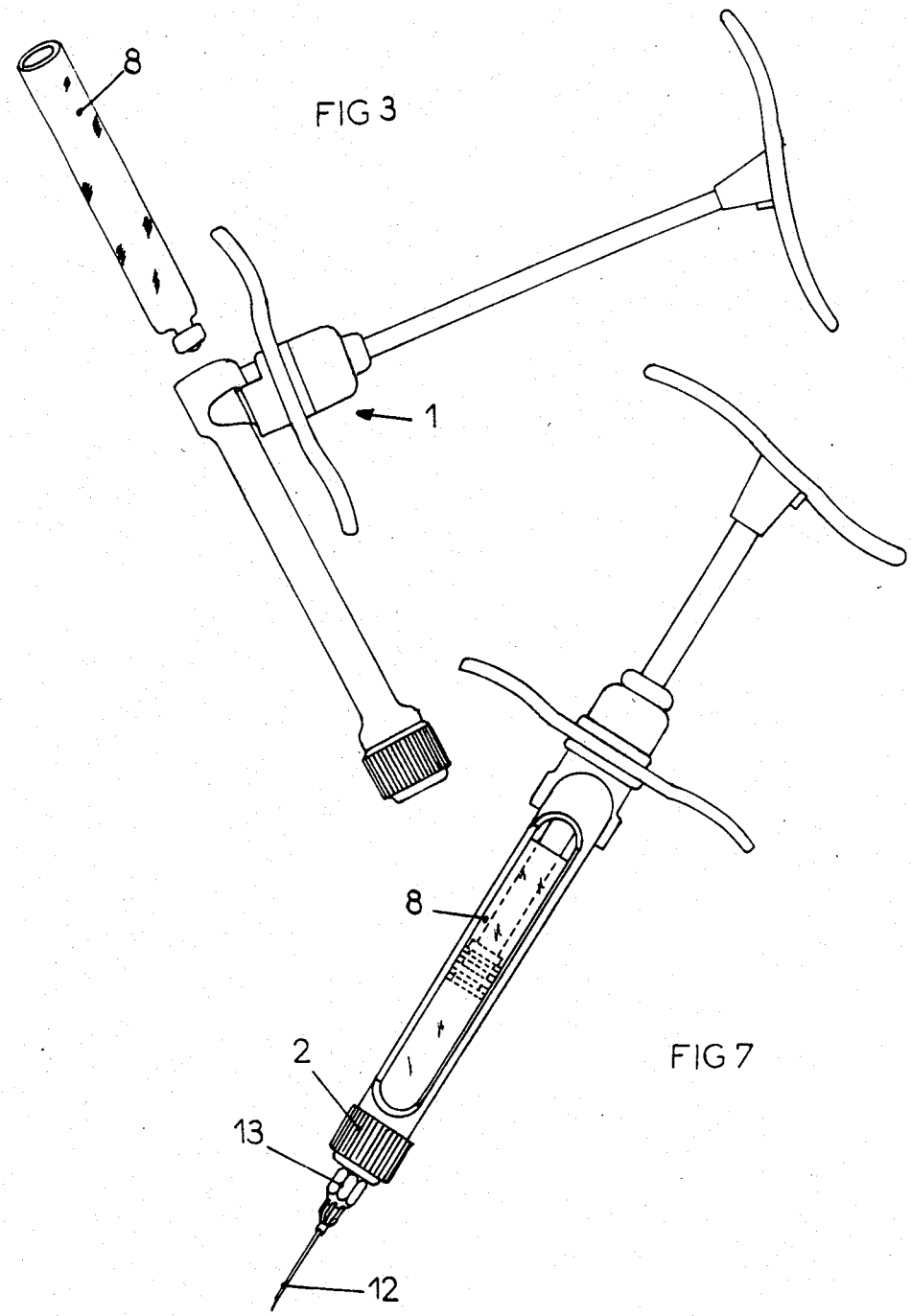
FIG. 3 is a perspective view of a syringe according to the present invention, ready to receive the cartridge.
FIG. 7 is a perspective view of the injection syringe of the present invention after it has been assembled, ready for use.

As seen in FIGS. 1-10, the lower end of the syringe of the present invention comprises a tubular sleeve 2 with a thread 3 on its inner surface. The main body 4 of the syringe has a bottom 5 having a central hole 6 capable of functioning as a stop at the periphery of the end 7 of a known type of cartridge 8. It is known that the cartridge contains, in its part 9, the fluid to be injected, while its sealing is ensured by the internal plug 10, which can work like a piston within a pressure-tight casing when it is pushed down by the plunger 21 of the syringe. The end 7 of the cartridge 8 is provided in the familiar way with a rubber protective cap 11.

Moreover, the improved injection syringe of the present invention is completed by a hollow needle 12 of a known type, joined to a plastic tip 13 which features a male threaded part 14 that extends so that it may be screwed into the tubular sleeve 2 of the syringe. The needle assembly 12 and its tip 13 is supplied in the familiar manner inside a sterile package containing a tube 15 closed by a removable plug 16.

According to another preferred feature of the invention, the needle 12 extends beyond the male part 14 of the threaded tip 13, for a distance 17 slightly less than the distance 19 separating the end of the tubular sleeve 2 and the sealing capsule 11 of the cartridge 8 when it is in place in the syringe 1.

Accordingly, the cartridge 8 is placed into the syringe 1, following the usual procedure as shown in FIG. 3. Once the syringe 1 has been closed, the package 15, 16 is opened and the needle assembly is taken by the tip 13 which is then positioned as shown in FIG. 4 in front of the sleeve 2 of the syringe. The male threaded part 14 is centered against the threaded interior 3 of the sleeve 2, to which it is then secured by screwing. It is only after having begun to screw the male threaded part 14 in that the upper end of the needle 12 comes in contact with the rubber plug 6 of the cartridge 8, which it then pierces as the screwing is completed. It is noted that throughout this procedure the operator has only touched the plastic tip 13, while the centering of the threaded part 14 on the tubular sleeve 2 prevents the upper end of the needle 12 from touching anything before piercing the plug 6.

When the assembly is ready for use as shown in FIG. 6, the needle 12 may be extracted and replaced by another one, without any need for the practioner to touch anything except the tip 13. Inversely, the needle 12 remains in position on the syringe 1 shown in FIG. 6, and therefore the practitioner may remove the cartridge 8 and replace it with another one without violating the regulation of asepsis.

Figure 8:
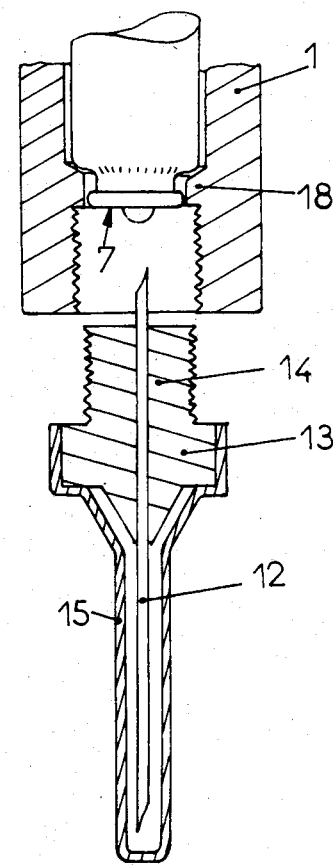
FIGS. 8 and 10 are cross-sectional views as in FIGS. 5 and 6 of several variations of the injection syringe of the present invention.

In the variation of the present invention, as shown in FIG. 8, the bottom 5 is replaced by a simple stop collar 18 against which the neck 19 of the cartridge 8 comes to rest. The end 7 of the cartridge 8 is now free over its entire surface to receive, after being screwed in, the support of the end 20 of the male threaded part 14. This support contributes to ensuring the resistance to internal pressure when the practitioner pushes down the plunger 21.

Figure 9:
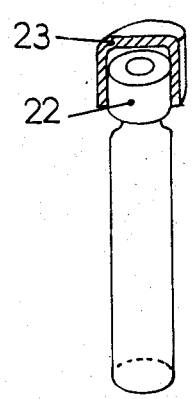

As shown in FIG. 9, a variation of the sterile packaging of the cartridge 8 of the present invention is disclosed. The end tip 22 is capped with a capsule 23 or a plastic sheath that the operator discards before use.

Figure 10:
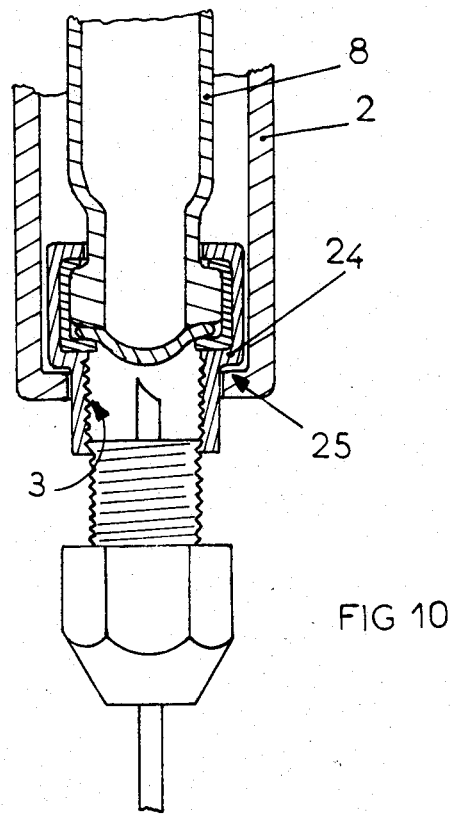

In the variation of FIG. 10, the tip 22 of the cartridge 8 is supplied with a fixed sleeve 24, comprising: an outer collar 25 that abuts against the interior of the syringe 2; and the inner threading 3 to receive the male threaded part 14 of the needle 12. Here, the needle 12 screws directly onto the cartridge 8 and the syringe 2 is used only to hold together the assembly and push back the piston 10.

The above description is included to illustrate the operation of the preferred embodiment and is not meant to limit the scope of the invention. The scope of the invention is to be limited only by the following claims. From the above discussion, many variations are apparent to one skilled in the art which would yet be encompassed by the spirit and scope of the invention.

I claim:
1. An improved injection syringe device, comprising:
housing means for containing fluid to be injected said housing means further comprising an upper and lower portion wherein said lower portion further comprises a lower surface having an aperture passing therethrough wherein said aperture is subtended by a plug centrally disposed across said aperture;
plunger means for ejecting said fluid operably connected to an upper portion of said housing means;
a one piece hollow member having external threads on a portion thereof having a uniform central bore passing therethrough for fixedly retaining a hollow injection needle said hollow injection needle extending beyond the end of an upper portion of said hollow member without the end of said extending portion of said needle penetrating through said plug until said hollow member is completely screwed into a tubular sleeve; and
tubular sleeve means having a recess at a lower one piece end thereof for accommodating and retaining said housing means therein and having an internally threaded end integrally formed therewith for close communication with said externally threaded hollow member said internally threaded end further comprising a flat upper portion having an aperture passing therethrough for receivabkly centering said hollow injection needle and tightly sealing said plug of said housing means against an upper surface of said flat upper portion of said internally threaded end thereby subtending said aperture passing through said flat upper portion of said internally threaded end and threaded side walls for receivably accommodating and closely communicating with said externally threaded hollow member.

* * * * *